US009890159B2

(12) United States Patent
Huijbregts et al.

(10) Patent No.: US 9,890,159 B2
(45) Date of Patent: Feb. 13, 2018

(54) PROCESS FOR MAKING DUOCARMYCIN PRODRUGS

(71) Applicant: SYNTHON BIOPHARMACEUTICALS B.V., Nijmegen (NL)

(72) Inventors: Tijl Huijbregts, Nijmegen (NL); Ronald Christiaan Elgersma, Nijmegen (NL); Patrick Henry Beusker, Nijmegen (NL); Johannes Albertus Frederikus Joosten, Nijmegen (NL); Rudy Gerardus Elisabeth Coumans, Nijmegen (NL); Henri Johannes Spijker, Nijmegen (NL); Wiro Menge, Nijmegen (NL); Franciscus Marinus Hendrikus De Groot, Nijmegen (NL)

(73) Assignee: Synthon Biopharmaceuticals B.V., Nijmegen (NL)

( * ) Notice: Subject to any disclaimer, the term of this patent is extended or adjusted under 35 U.S.C. 154(b) by 0 days.

(21) Appl. No.: 15/316,444

(22) PCT Filed: Jun. 5, 2014

(86) PCT No.: PCT/EP2014/061701
§ 371 (c)(1),
(2) Date: Dec. 5, 2016

(87) PCT Pub. No.: WO2015/185142
PCT Pub. Date: Dec. 10, 2015

(65) Prior Publication Data
US 2017/0145006 A1    May 25, 2017

(51) Int. Cl.
C07D 513/02    (2006.01)
C07D 471/04    (2006.01)
C07D 209/60    (2006.01)

(52) U.S. Cl.
CPC ......... C07D 471/04 (2013.01); C07D 209/60 (2013.01)

(58) Field of Classification Search
CPC .................... C07D 471/04; C07D 209/60
USPC .......................................... 546/121
See application file for complete search history.

(56) References Cited

U.S. PATENT DOCUMENTS

| 8,680,293 | B2 | 3/2014 | Beusker et al. |
| 8,889,868 | B2 | 11/2014 | Beusker et al. |
| 9,629,924 | B2 | 4/2017 | Beusker et al. |
| 2015/0216844 | A1 | 8/2015 | Beusker et al. |
| 2016/0052880 | A1 | 2/2016 | Beusker et al. |
| 2016/0324979 | A1 | 11/2016 | De Roo et al. |
| 2017/0080103 | A1 | 3/2017 | Ariaans et al. |

FOREIGN PATENT DOCUMENTS

| WO | WO 2009/017394 A1 | 2/2009 |
| WO | WO 2010/062171 A2 | 6/2010 |
| WO | WO 2011/133039 A2 | 10/2011 |
| WO | WO 2015/104359 A2 | 7/2015 |
| WO | WO 2015/177360 A1 | 11/2015 |
| WO | WO 2016/046173 A1 | 3/2016 |

OTHER PUBLICATIONS

Tietze et al,Enatio-and Diastereoselective Synthesis of Duocarmycine-Based Prodrugs for a Selective Treatment of Cancer by Epoxide Opening, Chem. European Journal, vol. 14, No. 3, p. 895-901.*
El-Faham, A. and Albericio, F., "Peptide Coupling Reagents, More than a Letter Soup," *Chemical Reviews* 111(10:6557-6602, American Chemical Society, United States (2011).
International Preliminary Report on Patentability (Chapter II of the Patent Cooperation Treaty) for International Application No. PCT/EP2014/061701, European Patent Office, Munich, Germany, completed on Sep. 6, 2016, including Chapter II Demand and Art. 34 amendments, 12 pages.
International Search Report and Written Opinion for International Application No. PCT/EP2014/061701, European Patent Office, Rijswijk, Netherlands, dated Nov. 6, 2014, 14 pages.
Larock, R.C., "Halogenation of Alcohols," in *Comprehensive Organic Transformations. A Guide to Functional Group Preparations*, 2$^{nd}$ Edition, pp. 689-693, Wiley-VCH, Germany (1999).

(Continued)

*Primary Examiner* — T. Victor Oh
(74) *Attorney, Agent, or Firm* — Sterne, Kessler, Goldstein & Fox P.L.L.C.

(57) ABSTRACT

The present invention relates to a process comprising converting a compound of formula (I) into a compound of formula (II) by reaction with an organolithium reagent, which compound can be further converted into duocarmycin analogs consisting of a DNA-alkylating and a DNA-binding part, and still further into corresponding antibody-drug conjugates.

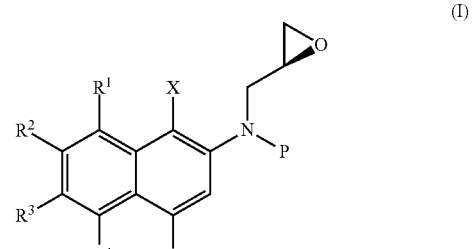

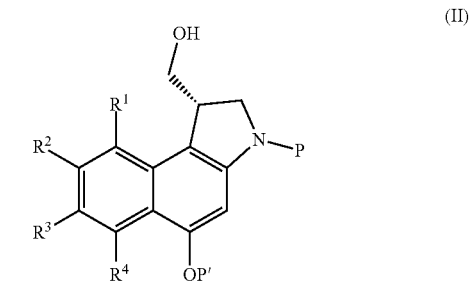

14 Claims, No Drawings

(56) References Cited

OTHER PUBLICATIONS

Tietze, L.F., et al., "Atropisomerism of Aromatic Carbamates," *Chemistry—A European Journal* 16(42):12678-12682, Wiley-VCH Verlag GmbH & Co., Germany (2010).

Tietze, L.F., et al., "Synthesis of Fluorescence-Labelled Glycosidic Prodrugs Based on the Cytotoxic Antibiotic Duocarmycin," *Eur. J Org. Chem.* 2010(36):6909-6921, Wiley-VCH Verlag GmbH & Co., Germany (2010).

Botman, P. N. M., et al., "Synthesis, Properties and Applications of BICAP: a New Family of Carbazole-Based Diphosphine Ligands," *Adv. Synth. Catal.* 346:743-754, Wilet-VCH. Verlag GmbH & Co., Germany (2004).

* cited by examiner

PROCESS FOR MAKING DUOCARMYCIN PRODRUGS

BACKGROUND OF THE INVENTION

The present invention relates to an improvement in the process for making antitumor antibiotic duocarmycin prodrugs. Such prodrugs can be used for selective treatment of cancer through antibody-directed enzyme prodrug therapy (ADEPT). The compounds are based on the cytotoxic antibiotics (+)-CC-1065, (+)-Duocarmycin A and (+)-Duocarmycin SA.

CC-1065 and duocarmycin analogues, which typically consist of a DNA-alkylating and a DNA-binding part, are known for their potent antitumor properties, but are normally not used on their own because of their extreme high toxicity. Nowadays they are being explored as cytotoxic drugs in antibody-drug conjugates (ADCs).

ADCs seem to have the potential to address the great unmet need for effective new treatments in cancer, which continues to be a major cause of death, by directing the highly potent cytotoxic drug specifically to cancer cells. Therefore, an industrial scale synthesis of duocarmycin prodrugs is one of the key aspects for the future commercial success of ADCs comprising duocarmycin analogues.

Various processes for making duocarmycin analogues and their intermediates, in particular for making the DNA-alkylating part of such analogues, are known in the prior art.

L. F. Tietze et al. in Chem. Eur. J. 2008, 14, 895-901 describe the enantio- and diastereoselective synthesis of duocarmycin-based prodrugs by epoxide opening. For the metal-mediated cyclisation of compound (1) to give compound (2) several different reaction conditions to give reasonable results had to be explored.

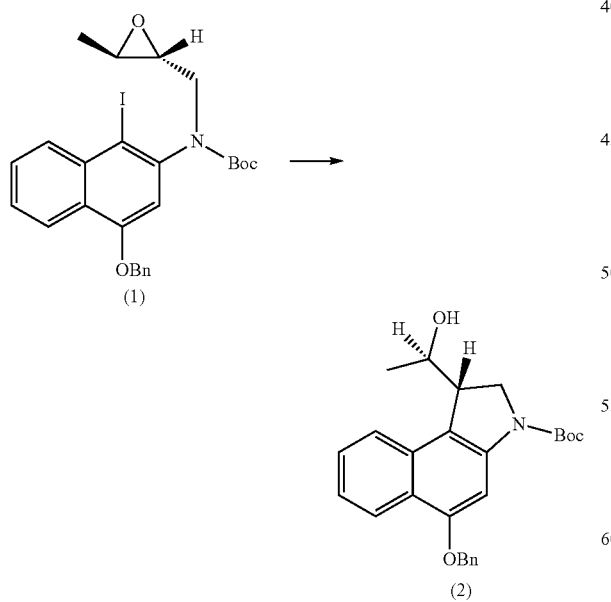

To achieve a stereoselective reaction, the authors concentrated on the use of lithium-containing cuprates as it was known that lithium tends to coordinate to the oxygen of the epoxide to allow the formation of a sterically fixed transition state, which is shown in Scheme 5 of said reference. The best results for the cyclisation reaction were achieved by using the copper organyl $Li_2Cu(CN)Me_2$ (78% yield) and the zinc organyl $Li_2Zn(SCN)Me_3$ (72% yield), whereas employing n-BuLi nearly exclusively afforded (47% yield) the dehalogenated product with only 7% of the desired five-membered ring product (2). See Table 2 in said reference.

L. F. Tietze et al. describe in Schemes 6 and 7 of the Eur. J. Org. Chem. 2010, 6909-6921 a metal-induced ring-closure of the epoxide tert-butyl (8-cyano-4-(benzyloxy)-1-bromo-naphthalen-2-yl)(oxiran-2-yl)carbamate to the desired enantiopure five-membered ring product using n-butyl lithium, but in a yield of only 12%. It is further mentioned that all other attempts to initiate the cyclisation via a zincate or cuprate failed.

Thus, while duocarmycin analogues and processes for making key intermediates of them are known in the prior art, there still exists a need for an improvement. In particular, it would be desirable to have an enantioselective process providing duocarmycin analogue intermediates in a good purity, acceptable yield and in a form which is well suitable for the next conversion steps into duocarmycin analogues having a DNA-alkylating part as well as a DNA-binding part and corresponding antibody-drug conjugates, which process does not require the use of intermetal reagents like the aforementioned expensive, hard-to-handle and not-readily-available lithium cuprates and -zincates.

SUMMARY OF THE INVENTION

The present invention relates to an improved process for making duocarmycin analogues, which is simple with respect to process conditions and provides the desired 5-membered ring-closed product in an acceptable yield.

In a first aspect, the present invention provides for a process comprising converting a compound of formula (I)

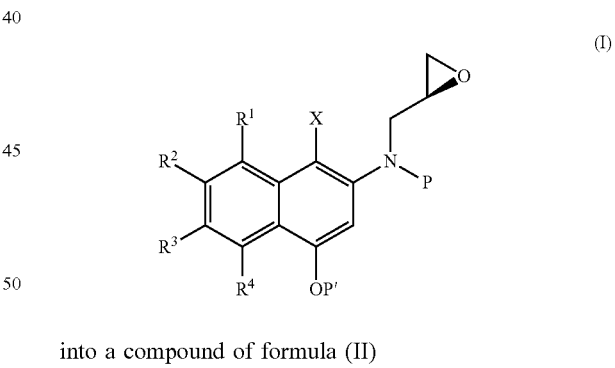

into a compound of formula (II)

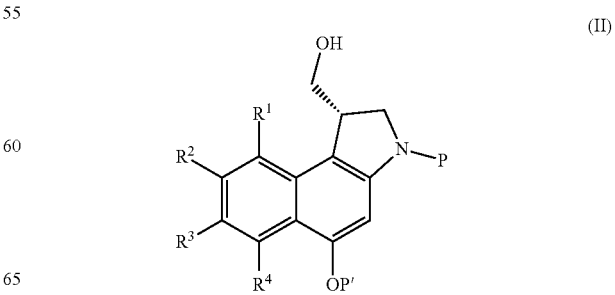

by reaction with an organolithium reagent, wherein P and P' are independently protective groups, $R^1$ is $CH_3$, $CH_2CH_3$, $OCH_3$, $OCH_2CH_3$, $CF_3$, $OCF_3$, Cl or F, $R^2$, $R^3$, $R^4$ are independently H or $C_{1-6}$ alkyl or $R^1$ and $R^2$ taken together form a 5- or 6-membered (hetero)cycloalkyl group and X is halogen.

In a preferred embodiment of the invention process, the organolithium reagent is selected from the group consisting of n-butyl lithium, tert-butyl lithium and methyl lithium.

In an embodiment of the present invention, $R^1$ is $CH_3$, $CH_2CH_3$, $OCH_3$ or $OCH_2CH_3$; $R^2$, $R^3$, $R^4$ are independently H or $C_{1-6}$ alkyl; or $R^1$ and $R^2$ taken together form a 5-membered (hetero)cycloalkyl group. Advantageously, $R^2$, $R^3$, $R^4$ are independently H or $CH_3$.

X advantageously is bromine or iodine.

In a second aspect, the invention provides for a process further comprising converting the compound of formula (II) into a compound of formula (III)

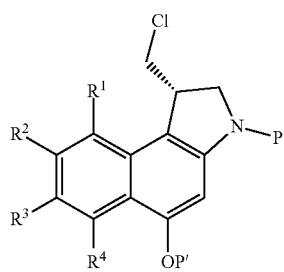

(III)

by either a one-step or two-step reaction with a chlorinating reagent, wherein $R^1$, $R^2$, $R^3$, $R^4$, P and P' have the meaning defined above.

In a preferred embodiment of the invention process, the chlorinating reagent is LiCl or $PPh_3/CCl_4$.

In a third aspect, the invention provides for a process further comprising converting the compound of formula (III) into a compound of formula (IV)

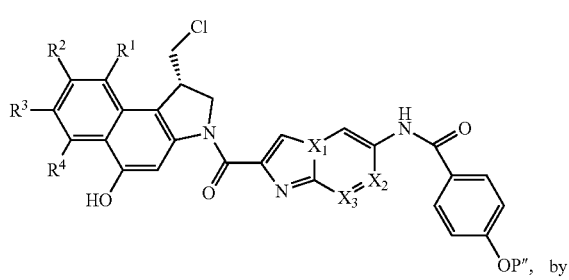

(IV)

by a) removal of the P protective group; and b) reaction with a compound of formula (V)

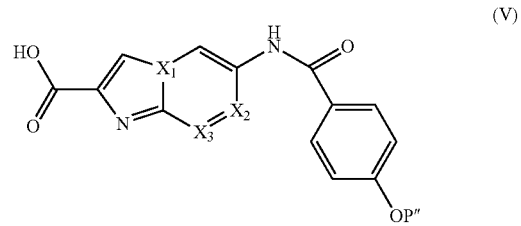

(V)

in the presence of a coupling reagent followed by c) elimination of the P' protective group, wherein $R^1$, $R^2$, $R^3$, $R^4$, P and P' have the meaning defined above, P''' is independently a protective group and $X_1$, $X_2$, $X_3$ are independently C or N.

In a preferred embodiment of the invention process, the coupling reagent is BOP, EDC, HATU or TBTU.

In an embodiment of the present invention, $X_1$ is N and $X_2$ and $X_3$ are C.

In a fourth aspect, the invention provides for the preparation of corresponding antibody-drug conjugates (ADCs) starting from a compound of formula (IV).

DETAILED DESCRIPTION OF THE INVENTION

The following detailed description is provided so that the subject invention may be more fully understood by those skilled in the art of duocarmycin prodrugs.

Definitions

Unless defined otherwise, all technical and scientific terms used herein have the same meaning as commonly understood by one of ordinary skill in the art.

The term "organolithium reagent" as used throughout the present specification is any chemical compound containing a bond between carbon and lithium. This definition does not include intermetal reagents such as the lithium cuprates and -zincates used in the prior art references cited above. In accordance with the present invention, the organolithium reagent is a monometal organolithium reagent. Advantageously, the monometal organolithium reagent is selected from the group consisting of n-butyl lithium, tert-butyl lithium and methyl lithium. N-butyl lithium is a particularly preferred monometal organolithium reagent.

The term "protective group" as used throughout the present specification is without limitation any group introduced into the molecule by chemical modification of a functional group in order to obtain chemoselectivity in a subsequent chemical reaction. In accordance with the present invention, an alcohol protective group (i.e. P' and P''') and an amine protective group (i.e. P) are used. Preferred alcohol protective groups are the benzyl group and the methoxymethyl ether group. A preferred amine protective group is the tert-butyloxycarbonyl group. However, many other suitable alcohol- and amine-protective groups are known to the person skilled in the art as illustrated by Peter G. M. Wuts and Theodora W. Greene in Greene's Protective Groups in Organic Synthesis, Fourth Edition, 2006 (ISBN: 978-0-471-69754-1) and many of these can be used in the process in accordance with the present invention. The person skilled in the art will be able to select from said reference suitable protective groups to be used in accordance with the process of the present invention.

The term "5- or 6-membered (hetero)cycloalkyl group" as used throughout the present specification is a cyclopentane or cyclohexane ring which is formed from $R^1$ and $R^2$ and the carbon atoms to which these substituents are attached, in which optionally one or more carbon atoms are hetero atoms, preferably O.

The term "chlorinating reagent" as used throughout the present specification is without limitation any reagent able to substitute either in one-step or two-steps the hydroxy group with a chlorine atom. Examples of suitable chlorinating reagents can be found in Comprehensive Organic Transformations, A Guide to Functional Group Preparations, Second Edition, 1999, pages 690-693 (ISBN 0-471-19031-4), authored by Richard C. Larock. Advantageously, in the case the substitution is performed after transformation of the hydroxy group into a leaving group L (see Scheme 1 below, route A), said chlorinating reagent is selected from the group consisting of LiCl, KCl, NaCl, $NH_4Cl$, HCl, and $AlCl_3$ in concentrated HCl. A preferred chlorinating reagent is LiCl. Alternatively, in the case the substitution is performed directly on the hydroxy group (see Scheme 1 below, route B), said chlorinating reagent advantageously is selected from the group consisting of $PPh_3/CCl_4$, $PPh_3/NCS$, $SOCl_2$, and $PCl_3/PCl_5$. A preferred chlorinating reagent is $PPh_3/CCl_4$.

The term "coupling reagent" as used throughout the present specification is without limitation any peptide coupling reagent known to the person skilled in the art. Suitable examples are described by Ayman El-Faham and Fernando Albericio in Peptide Coupling Reagents, more than a Letter Soup in Chem. Rev. 2011, 111, 6557-6602. Advantageously, said coupling reagent is selected from the group consisting of BOP, DCC, DIC, EDC, HATU, TBTU and T3P. In a preferred embodiment of the invention process, the coupling reagent is BOP, EDC, HATU or TBTU. A more preferred peptide coupling reagent is EDC.

The following abbreviations are used herein and have the indicated definitions: Bn: benzyl; DCM: dichloromethane; DIPEA: N,N-diisopropylethylamine; DMA: N,N-dimethylacetamide; DMF: N,N-dimethylformamide; DMSO: dimethyl sulfoxide; NMP: 1-methyl-2-pyrrolidinone; HMPA: hexamethylphosphoramide; NCS: N-chloro succinimide; BOP: benzotriazol-1-yloxytris(dimethylamino)phosphonium hexafluorophosphate; DIC: N,N'-diisopropylcarbodiimide; DCC: N,N'-dicyclohexylcarbodiimide; EDC: 1-[(3-dimethylaminopropyl)]-3-ethylcarbodiimide hydrochloride; EtOAc: ethyl acetate; HATU: O-(7-azabenzotriazol-1-yl)-1,1,3,3-tetramethyluronium hexafluorophosphate; TBTU: O-(benzotriazol-1-yl)-1,1,3,3-tetramethyluronium tetrafluoroborate; T3P: 1-propanephosphonic anhydride solution, 2,4,6-tripropyl-1,3,5,2,4,6-trioxatriphosphorinane-2,4,6-trioxide solution; Ms: methanesulfonyl; RT: room temperature; TFA: trifluoroacetic acid; THF: tetrahydrofuran; p-TsOH: p-toluene sulfonic acid; $NH_4HCO_2$: ammonium formate.

In accordance with the present invention, it was found with surprise that the compound of formula (II) may be advantageously prepared from a compound of formula (I) by reaction with an organolithium reagent in a suitable solvent in an acceptable yield despite the teachings in the prior art. In a preferred embodiment of the present invention, a strong base like sodium methoxide or sodium borohydride is added to the suitable solvent.

A suitable solvent for the enantioselective ring-closure of a compound of formula (I) into a compound of formula (II) is without limitation an organic solvent, preferably an aprotic solvent. A preferred solvent is an ether solvent, and a particularly preferred solvent is THF.

The process according to the various aspects of the present invention is shown in Scheme 1 below, wherein P and P' are independently protective groups; $R^1$ is $CH_3$, $CH_2CH_3$, $OCH_3$, $OCH_2CH_3$, $CF_3$, $OCF_3$, Cl or F; $R^2$, $R^3$, $R^4$ are independently H or $C_{1-6}$ alkyl; or $R^1$ and $R^2$ taken together form a 5- or 6-membered (hetero)cycloalkyl group; and X is halogen.

In a preferred embodiment of the present invention, $R^1$ is $CH_3$, $CH_2CH_3$, $OCH_3$ or $OCH_2CH_3$; $R^2$, $R^3$, $R^4$ are independently H or $C_{1-6}$ alkyl; or $R^1$ and $R^2$ taken together form a 5-membered (hetero)cycloalkyl group. X advantageously is bromine or iodine.

Scheme 1

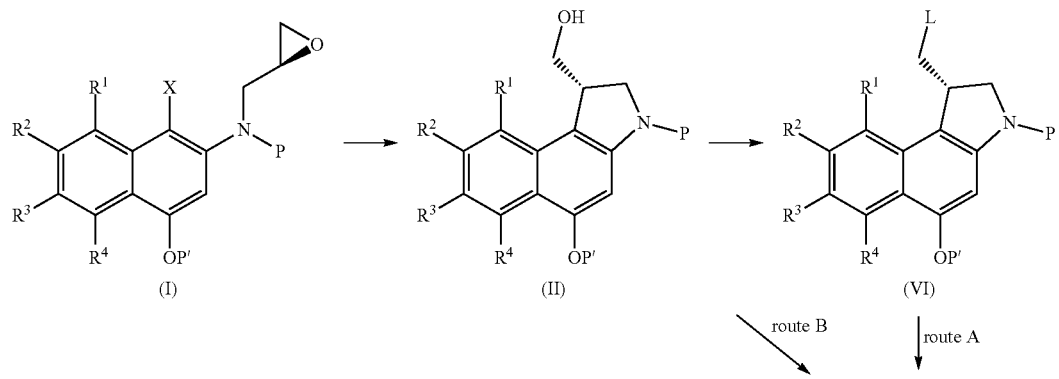

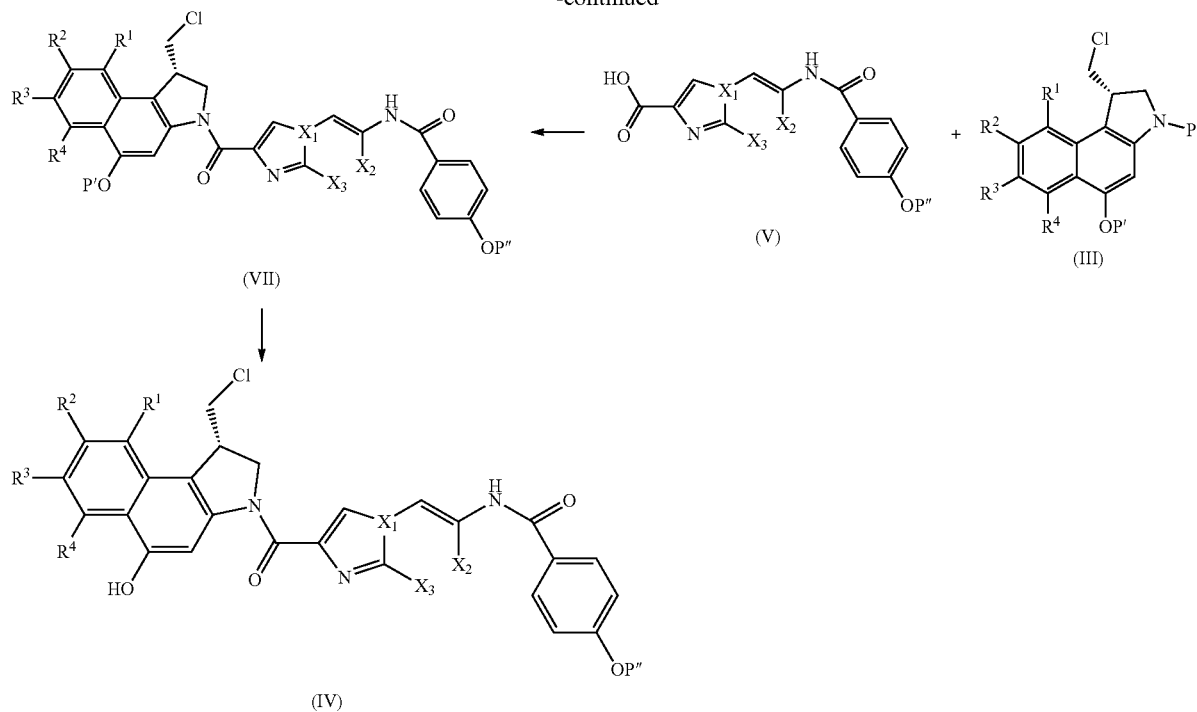

The starting material of the present invention, i.e. a compound of formula (I) may be produced by or analogous to any suitable process known in the prior art, e.g. the one described by L. F. Tietze et al. in Eur. J. Org. Chem. 2010, 6909-6921 in Schemes 3-6.

Preferred starting material compounds of formula (I) are the following compounds:

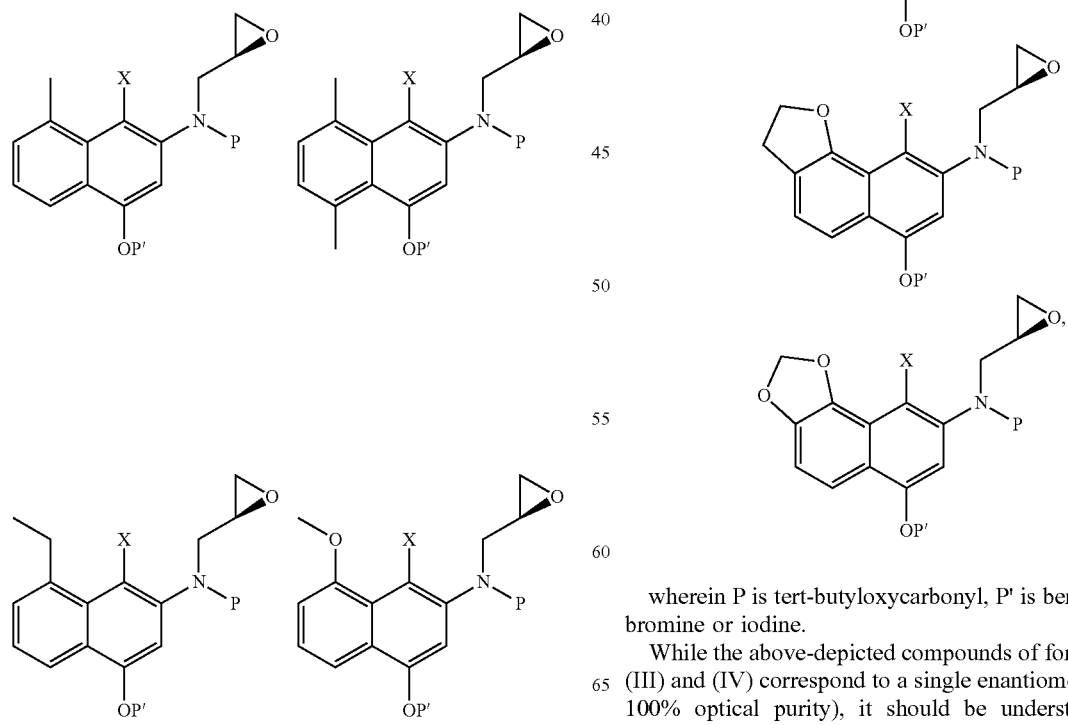

wherein P is tert-butyloxycarbonyl, P' is benzyl, and X is bromine or iodine.

While the above-depicted compounds of formula (I), (II), (III) and (IV) correspond to a single enantiomer (i.e. having 100% optical purity), it should be understood that the present invention also covers compounds having an optical purity lower than 100%, whenever relevant. It is however preferred that the compound of formula (I), (II), (III) and (IV) is of an optical purity of at least 95% or higher, preferably 98% or higher, most preferably 99% or higher.

If desired or advantageous, the compound of formula (II) may be isolated from the reaction mixture as such as a single enantiomer, and optionally may be purified.

In a specific embodiment of the present invention, the compound of formula (II) is not purified after reaction of a compound of formula (I) with an organolithium reagent, but is directly further converted into a compound of formula (VI) in which the OH group advantageously is transformed into a leaving group L (see Scheme 1). L is any suitable leaving group known to the person skilled in the art. Advantageously, L is a sulfonate group such as mesylate, tosylate or besylate. Preferably, L is mesylate.

Subsequently, the compound of formula (VI) is converted into a compound of formula (III) by reaction with a chlorinating reagent in a suitable solvent.

Advantageously, said chlorinating reagent is selected from the group consisting of LiCl, KCl, NaCl, NH$_4$Cl, HCl, and AlCl$_3$ in concentrated HCl. A preferred chlorinating reagent for the preferred two-step conversion of a compound of formula (II) into a compound of formula (III) is LiCl.

A suitable solvent for the chlorination reaction is an organic solvent, preferably a polar aprotic solvent. A preferred solvent is DMF.

Preferred compounds of formula (III) are the following compounds:

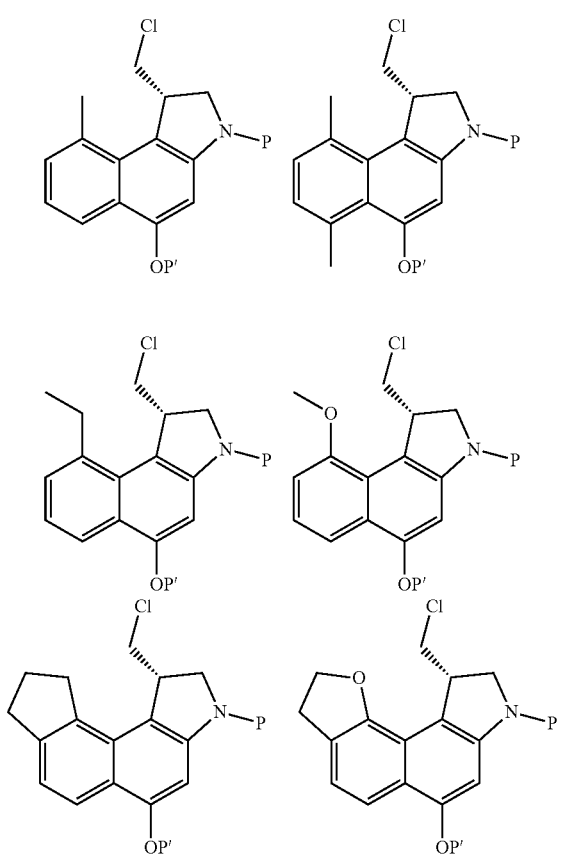

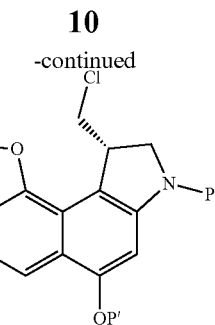

Alternatively, the compound of formula (II) may be directly converted to a compound of formula (III) by reaction with a chlorinating reagent selected from the group consisting of PPh$_3$/CCl$_4$, PPh$_3$/NCS, SOCl$_2$, and PCl$_3$/PCl$_5$. A preferred chlorinating reagent for the one-step conversion of a compound of formula (II) into a compound of formula (III) is PPh$_3$/CCl$_4$.

In a further specific embodiment of the present invention, in an advantageous mode of making the compound of formula (VII) in accordance with the present invention, as depicted in Scheme 1, the compound of formula (III) is first treated with acid to remove the P protective group, and then the product is reacted with a compound of formula (V) in a suitable solvent in the presence of a coupling reagent providing a compound of formula (VII). In one embodiment, a base is added to the suitable solvent. Suitable bases are tertiary amines. A particularly suitable base is DIPEA.

Advantageously, the acid is an inorganic mineral acid, for example HCl.

A suitable solvent for use in the peptide coupling reaction is an organic solvent, preferably a polar aprotic solvent. Advantageously, said suitable solvent is selected from the group consisting of DMA, DMF, DMSO, NMP, HMPA, methyl ethyl ketone, acetonitrile, THF, DCM, acetone, EtOAc, and 2-butanone. A preferred solvent is DMA.

Advantageously, the coupling reagent is a coupling reagent conventionally used in peptide coupling. Preferably, said coupling reagent is selected from the group consisting of BOP, DCC, DIC, EDC, HATU, TBTU and T3P, more preferably BOP, EDC, HATU or TBTU. A particularly preferred coupling reagent is EDC.

Subsequently, the compound of formula (VII) is converted into a compound of formula (IV) by elimination of the protective group P' in a suitable solvent, preferably by hydrogenolysis in case P' is a benzyl group.

Advantageously, the hydrogenolysis is conducted catalytically in the presence of a hydrogenation metal catalyst, preferably palladium on carbon and a hydrogen source. Advantageously, the hydrogen source is hydrogen or ammonium formate. The preferred hydrogen source for the hydrogenolysis is ammonium formate.

The compound of formula (IV) typically is a solid product and the isolated product is a stable material, which may be stored at ordinary conditions of storage and advantageously is used in the synthesis of corresponding antibody-drug conjugates (ADCs) using procedures and equipment well-known to a person skilled in the art and as described e.g. in WO2010/062171A and WO2011/133039A.

The following examples are intended to illustrate the scope of the present invention but not to limit it thereto.

EXAMPLES

Example 1

General Procedure for the Preparation of Compounds of Formula (II)

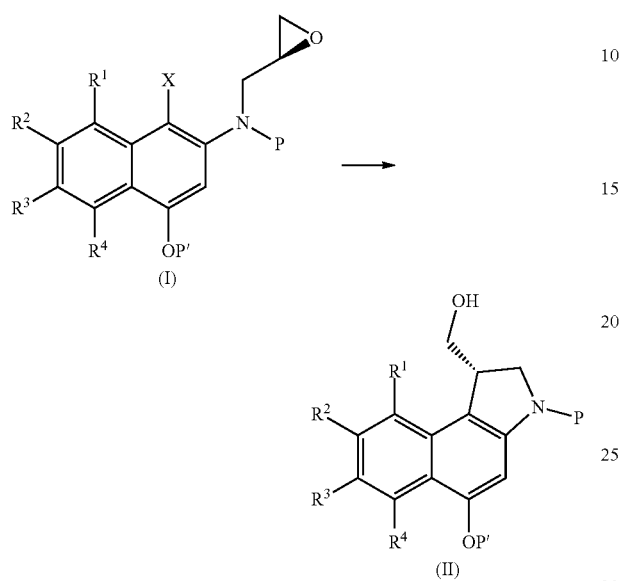

A compound of formula (I) is dissolved in dry THF and cooled to −20° C. under an argon atmosphere. Next, n-butyl lithium (1.1 equivalents) is added dropwise at −20° C. and stirred until completion. The reaction is then quenched using a saturated aqueous solution of ammonium chloride. The obtained reaction mixture is extracted twice with EtOAc and the organic layers are combined. Then, option 1, the organic layer is dried using a drying agent and concentrated, optionally followed by purification using, for example, silica gel chromatography to obtain the product compound of formula (II). Or, option 2, to the organic layer an amount (for example 0.15 equivalents) of p-TsOH and water is added and the mixture is stirred for 60 minutes. The side-product degrades and is more easily separated from the desired compound of formula (II). This is followed by extraction with a 1M aqueous $Na_2CO_3$ solution, a saturated NaCl solution and drying of the organic layer, followed by concentration to obtain the crude product of formula (II). The crude product optionally can be purified, for example by silica gel chromatography.

Example 2a

Preparation of compound (12), a compound according to formula (II), from compounds (3) and (4) according to the following reaction scheme:

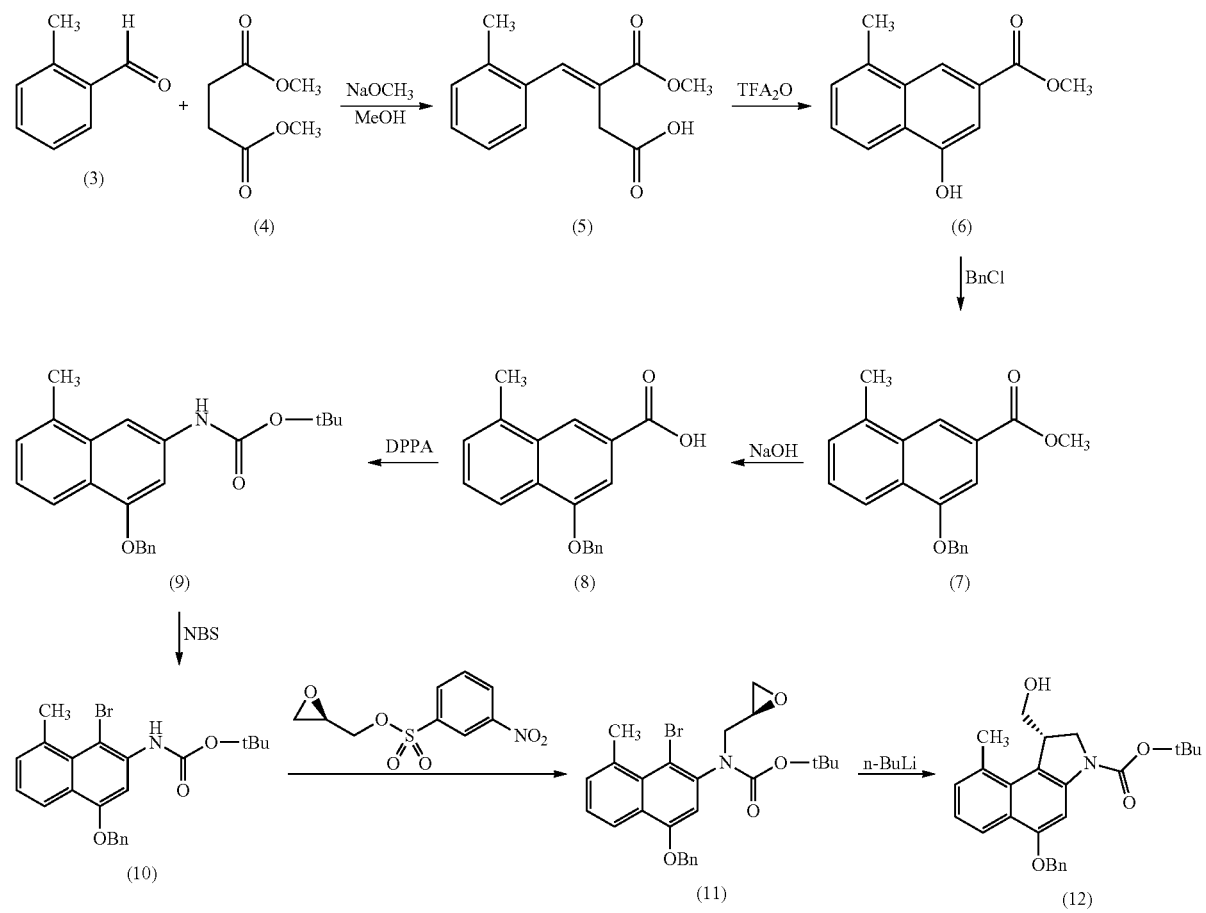

2-Methylbenzaldehyde (3) (1.5 kg) and dimethyl succinate (4, 1.75 equivalents) were reacted in the presence of methanolic sodium methoxide (1.3 equivalents) in methanol (approx. 4 l) at 65-80° C. for 1 hour. Then, the mixture was cooled to 20° C., the excess of base was neutralized with HCl, diluted with water, and unreacted dimethyl succinate was removed by extraction with DCM. The mixture was acidified with excess of HCl and the product was extracted in DCM. This extract was dried over $MgSO_4$. The solvent was changed from DCM to THF on a rotary evaporator under vacuum (80 mbar, bath 40-60° C.) providing a solution of crude (E)-3-(methoxycarbonyl)-4-(o-tolyl)but-3-enoic acid (5) in THF (10 l).

This solution of compound (5) was then reacted with trifluoroacetic anhydride (2.49 kg) at reflux temperature to a complete conversion into methyl 4-hydroxy-8-methyl-2-naphthoate (6). The reaction mixture was neutralized with an aqueous $K_2CO_3$ solution. The product was extracted with EtOAc, dried with $MgSO_4$, concentrated and crystallized by cooling to –5° C. The crystals (white/yellow) were filtered, washed with acetonitrile and dried at 48-53° C. for 16 hr providing compound (6) in an amount of 1119 g (41.4% yield, purity 99.8%).

Methyl 4-hydroxy-8-methyl-2-naphthoate (6) (0.83 kg) was treated with benzyl chloride (1.05 equiv.) in DMF (3.3 l) at 50-80° C. in the presence of $K_2CO_3$ (1.4 equiv.).

When the reaction was complete, the mixture was cooled to 50° C., diluted with DCM, cooled to 20° C. and water was added. The organic layer was separated and the wet extract was concentrated by distillation under atmospheric pressure and then under vacuum to remove DMF. The residue comprising the intermediate methyl 4-(benzyloxy)-8-methyl-2-naphthoate (7) was diluted with toluene (5 l) and MeOH (6.6 l) and was treated with aqueous NaOH (1.24 kg (approx. 8 equiv.) in 7.6 l of water) solution under reflux for 2 hours. Water (29 l) was gradually added in several portions and methanol and toluene were removed by distillation. The volume of solution was about 32-33 l after solvent changeover to water. The crude 4-(benzyloxy)-8-methyl-2-naphthoic acid (8) was precipitated by addition of excess of 4M HCl (3.32 l), the suspension was cooled to 10° C. and the precipitate was filtered off, washed with water (30 l of 10° C.) and dried at 70° C. for 16 hours. Pure 4-(benzyloxy)-8-methyl-2-naphthoic acid (8) was obtained by crystallization from toluene (29.4 l) as off-white crystals. Precipitated crystals were filtered, washed with toluene and dried at 103-108° C. for 16 hr (956 g, 92.5% yield, purity 99.9%).

4-(Benzyloxy)-8-methyl-2-naphthoic acid (8) (1 kg) was reacted with diphenyl-phosphoryl azide (1.16 equivalents) in toluene (5 l) containing excess of tert-butanol (2.6 equivalents) in the presence of $Et_3N$ (1.1 equivalents) at 82-88° C. for ~3 hours. After cooling to 30° C., the reaction mixture was partitioned between EtOAc and water. The organic layer was separated, washed with an aqueous $Na_2CO_3$ solution, brine and dried over magnesium sulfate. EtOAc was distilled off and the crude product was triturated with isopropanol. Triturated crystals were filtered, washed with isopropanol and dried at 62-68° C. for 16 hr providing pure tert-butyl (4-(benzyloxy)-8-methylnaphthalen-2-yl)carbamate (9) in an amount of 1096 g (92.8% yield, purity 99.6%).

Tert-butyl (4-(benzyloxy)-8-methylnaphthalen-2-yl)carbamate (9) (1.05 kg) was treated with 1.05 equivalents of N-bromosuccinimide in THF (17.6 l) at –10° C. The reaction was quenched by addition of an aqueous $Na_2SO_3$ solution followed by 1 M sodium hydroxide solution. Ethyl acetate was added and the product (10) was extracted into organic layer. The extract was washed with brine, dried with $MgSO_4$ and evaporated to dryness on a rotary evaporator under vacuum. The crude intermediate tert-butyl (4-(benzyloxy)-1-bromo-8-methylnaphthalen-2-yl)carbamate (10) was dissolved in THF (3.3 l), deprotonated with potassium tert-butoxide (1.3 equivalents) at approx. 10° C. and alkylated with (S)-glycidyl nosylate (1.2 equivalents) at approx. 25° C. for 3 hours. The reaction was quenched by adding an aqueous $NH_4Cl$ solution and the reaction mixture was extracted with EtOAc. The EtOAc layer was washed with water and brine. Crude (S)-tert-butyl (4-(benzyloxy)-1-bromo-8-methylnaphthalen-2-yl)(oxiran-2-ylmethyl)carbamate (11) was obtained after evaporation of solvents. Crystallization from heptane gave 1185 g of pure (S)-tert-butyl (4-(benzyloxy)-1-bromo-8-methylnaphthalen-2-yl) (oxiran-2-ylmethyl)carbamate (11) as beige crystals in 82.3% yield (purity 96.09%).

(S)-tert-butyl (4-(benzyloxy)-1-bromo-8-methylnaphthalen-2-yl)(oxiran-2-ylmethyl)-carbamate (11) (1034 g) was dissolved in THF (10.4 l). The solution was cooled to –25° C. under an atmosphere of dry nitrogen. Then, n-butyl lithium (1 l; 2.5M in hexanes) was added gradually keeping the temperature at –25 to –20° C. and was stirred for an additional 10 minutes. The reaction mixture was quenched with saturated aqueous ammonium chloride (366 g in 1.1 l) and the water layer was extracted with ethyl acetate (2×4.8 l). The combined organic layers were stirred under vacuum for 20 minutes. Subsequently, an aqueous solution of p-TsOH (121 g PTSA monohydrate in 520 ml water) was added and the reaction mixture was stirred for 1 hour. The reaction was quenched by addition of 1M sodium carbonate solution. The water layer was discharged. The organic layer was washed with brine, dried over magnesium sulfate and evaporated to dryness.

One half of the crude (S)-tert-butyl 5-(benzyloxy)-1-(hydroxymethyl)-9-methyl-1H-benzo[e]indole-3(2H)-carboxylate (12) was dissolved in 2.13 l of DCM and was filtered over 2.4 kg of silica gel 60 Å, particle size 0.063-0.1 mm. The (side-) products were eluted with DCM (11 l) followed by DCM/Ethyl acetate (9:1; 13.4 l) and DCM/Ethyl acetate (8:2; 12 l). This procedure was repeated with the remaining half of crude compound and the fractions containing compound (12) were combined, concentrated, dried in vacuo and crystallized in DCM/pentane (4 ml/60 ml per g of residue) and dried under vacuum at 35-40° C. for 12-16 hours to give (S)-tert-butyl 5-(benzyloxy)-1-(hydroxymethyl)-9-methyl-1H-benzo[e]indole-3(2H)-carboxylate (12) as a beige to white solid (347 g, 39.9% yield, purity 96.3%, (R)-tert-butyl 5-(benzyloxy)-1-(hydroxymethyl)-9-methyl-1H-benzo[e]indole-3(2H)-carboxylate 5.14% yield).

Example 2b

Preparation of compound (12), a compound according to formula (II), from compound (9) according to the scheme of Example 2a:

Tert-butyl (4-(benzyloxy)-8-methylnaphthalen-2-yl)carbamate (9) (10.5 g) was treated with 1.01 equivalents of N-bromosuccinimide (5.20 g) in THF (31.5 g) at –10° C. The reaction was quenched by addition of an aqueous sodium hydroxide solution (0.75 g NaOH and 7.5 g water). The extract was washed with a saturated aqueous NaCl solution (15 g) and the water layer was extracted with ethyl acetate (11.25 g). The organic layers were combined, washed with a saturated aqueous NaCl solution (15 g) and concentrated under vacuum to yield tert-butyl (4-(benzyloxy)-1-bromo-8-methylnaphthalen-2-yl)carbamate (10) (14.36 g, 112.36% yield).

The crude intermediate (10) (14.36 g) was dissolved in THF (15 g) and toluene (10 g), deprotonated with potassium tert-butoxide which was added in two portions (1×4.30 and 1×0.20 g, 1.39 equivalents in total) at approximately 10° C. and alkylated with (S)-glycidyl nosylate (8.80 g, 1.19 equivalents) at approximately 25° C. for 2 hours. The reaction was diluted with toluene (37.5 g) and filtered with active carbon (0.75 g) over Kieselguhr™. The solid residue was washed with toluene (30 g) and the filtrate was washed with a saturated aqueous NaCl solution (2×15 g) and concentrated under vacuum to yield (11) as an oil (13.75 g, 95.49% yield).

The oil (11) (13.75 g) was dissolved in THF (135 g). The solution was cooled to −10° C. under an atmosphere of dry nitrogen. Then, sodium methoxide (1.50 g, 1.06 M) and n-butyl lithium (8.40 g, 1.16 M, 2.5M in hexanes) were added gradually at −10° C. under stirring. After an additional 80 minutes of stirring, the reaction mixture was quenched with a saturated aqueous NaCl solution (15 g) and water (9.75). The organic layer was subjected first to an acidic washing done using a mixture of aqueous acetic acid (0.30 g acetic acid and 2.70 g water) and a saturated NaCl solution (15 g of solution). This was followed by an alkaline washing with a mixture of a saturated aqueous NaHCO₃ solution (11.25 g of solution) and a saturated aqueous NaCl solution (11.25 g of solution).

After carbon filtration, the active carbon (1.12 g) on filter was washed with EtAc (15 g). The filtrate was evaporated to dryness (11.20 g) and dissolved in hot (55° C.) methyl tert-butylether (33.75 g). The solution was cooled to approximately 45° C. The suspension was diluted with methyl tert-butyl ether (22.5 g) and gradually cooled to −15° C., filtered, washed with methyl tert-butyl ether (2×5 g) and dried under vacuum giving (12) (5.40 g, 49.35% yield from compound (11), purity 99.56%).

Example 3a

Preparation of compound (14) from compound (12) according to the following scheme

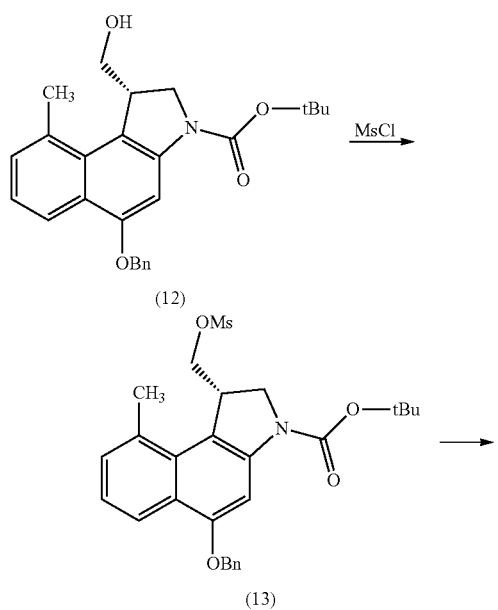

(S)-tert-butyl 5-(benzyloxy)-1-(hydroxymethyl)-9-methyl-1H-benzo[e]indole-3(2H)-carboxylate (12) (170 g; 405 mmol) was treated with methanesulfonyl chloride (1.3 equivalents) in DCM (1.4 l) in the presence of Et₃N (2.6 equivalents) for 90 minutes at 0-5° C. The reaction mixture was washed with hydrochloric acid, water and brine. The extract was dried over magnesium sulfate and evaporated to dryness. After solvent evaporation, the residue comprising the intermediate (S)-tert-butyl 5-(benzyloxy)-9-methyl-1-(((methyl-sulfonyl)oxy)methyl)-1H-benzo[e]indole-3(2H)-carboxylate (13) was dissolved in DMF (1.2 l) and treated with lithium chloride (5 equivalents) at approx. 80° C. for 90 min. After evaporation of DMF (8-4 mbar) the residue was partitioned between DCM and water. The lower layer was separated, washed with brine and dried over magnesium sulfate. DCM was then evaporated and the residue was dissolved in hot heptane (3.5 l), treated with activated carbon and filtered into a 4l jacketed reactor. The activated carbon on filter was washed with another portion of heptane. The solution of crude product was cooled to approx. 50° C., seeded and kept at this temperature for 1 hr. The suspension was cooled to 7° C. during 2 hrs, stirred for another hour at this temperature, filtered, washed with heptane and dried under vacuum. Dried crystals (135 g; 76%) were recrystallized from heptane using the procedure described above giving (S)-tert-butyl 5-(benzyloxy)-1-(chloromethyl)-9-methyl-1H-benzo[e]indole-3(2H)-carboxylate (14) (111 g; 82%, optical purity 99.99%; (63.0% overall yield)).

Example 3b

Preparation of compound (14) from compound (12) according to the scheme of Example 3a:

Compound (12) (10 g) was treated with methanesulfonyl chloride (3.0 g, 1.1 equivalents) in THF (50 g) in the presence of Et₃N (3.3 g, 1.37 equivalents) for 90 minutes at 0-5° C. The reaction mixture was quenched by addition of aqueous hydrochloric acid (1.70 g HCl 36% and 10 g water). The organic layer was washed with a saturated aqueous NaHCO₃ solution (5 g) and with a saturated aqueous NaCl solution (5 g). The water layer was extracted with ethyl acetate (13.3 g). The organic layers were combined and washed with a saturated aqueous NaCl solution (10 g) and was then concentrated under vacuum to yield (13) (13.10 g).

The residue comprising the intermediate (13) was dissolved in DMF (20 g) and treated with lithium chloride (2.40 g, 2.38 equivalents) at approximately 80° C. for 180 min. After cooling to 40° C., the reaction mixture was diluted with toluene (30 g) and water (50 g). The organic layer was separated, water (50 g) was added to the organic layer and this mixture was extracted with toluene (2×15 g). The combined organic layer was washed with a saturated aqueous NaCl solution (25 g) and then with water (25 g).

After carbon filtration, the active carbon (0.83 g) on filter was washed with toluene (11.7 g). The filtrate was evaporated to dryness (8.3 g) and was dissolved in a hot (60° C.) mixture of heptane (33.3 g) and ethanol (33.3 g). The solution gradually was cooled to −15° C., filtered, washed with heptane (2×8 g) and dried under vacuum at 60° C. (1 h) giving (14) (7.60 g, 72.80% related to compound (12), purity 99.36%, optical purity 99.99%)

Example 4

Preparation of 4-(Methoxymethoxy)Benzoic Acid for Use in Example 5

1 g (6.6 mmol) of methyl-4-hydroxybenzoate was dissolved in 25 ml DCM under a nitrogen atmosphere. Next, the solution was cooled to 0° C. followed by addition of 600 μl (7.9 mmol) chloromethyl methyl ether and 3.25 ml (19.7 mmol) DIPEA. The mixture was stirred and allowed to warm to room temperature overnight. The next day, water (100 ml) was added and the mixture was extracted twice with DCM (100 ml). The combined DCM layers were washed with brine (100 ml), dried with $Na_2SO_4$ and concentrated in vacuo to give 4-(methoxymethoxy)benzoic acid methyl ester.

The crude 4-(methoxymethoxy)benzoic acid methyl ester was dissolved in 10 ml MeOH followed by addition of 4 ml 4M NaOH solution. The mixture was heated at 70° C. for 4 h. TLC indicated complete conversion. The mixture was cooled to 0° C. and 100 ml 0.5 M $KHSO_4$ solution was added (pH=3) and extracted with EtOAc (2×75 ml). The combined EtOAc layers were dried with $Na_2SO_4$ and concentrated in vacuo to give 1 g (84%) of 4-(methoxymethoxy) benzoic acid as a white solid.

Example 5

Preparation of compound (15) from compound (18) and (19) according to the following reaction scheme:

Afterwards, the reaction mixture was concentrated, water (300 ml) was added and the resulting suspension was filtered. The solid residue was washed with $Et_2O$ (600 ml) and dried to yield ethyl 6-nitroimidazo[1,2-a]pyridine-2-carboxylate (20) (75 g, 319 mmol, 89% yield) as a sand coloured solid. UPLC-MS confirmed that the desired product was obtained.

A suspension of ethyl 6-nitroimidazo[1,2-a]pyridine-2-carboxylate (20) (20 g, 85 mmol) in MeOH (200 ml) was cooled to 0° C., 12M hydrogen chloride (70 ml, 850 mmol) was added drop wise followed by portion wise addition of zinc (22.3 g, 340 mmol). The reaction mixture was stirred for 30 minutes.

Next, MeOH (140 ml) was added and the reaction was quenched with concentrated $NH_3$ (15 equiv.) and filtered. The solid residue was washed with MeOH (2×25 ml). The filtrate was concentrated and re-suspended in $CHCl_3$ (700 ml), $H_2O$ (300 ml) and concentrated $NH_3$ (300 ml, 35% solution). This mixture was stirred until everything was dissolved. The layers were separated and the water layer was extracted once with $CHCl_3$. The organic layers were combined, washed with a saturated aqueous NaCl solution (50 ml), dried over $MgSO_4$, filtered and concentrated in vacuo to yield ethyl 6-aminoimidazo[1,2-a]pyridine-2-carboxylate (21) (11.8 g, 68%) as a grey/green solid. UPLC-MS confirmed that the desired product was obtained.

To a solution of ethyl 6-aminoimidazo[1,2-a]pyridine-2-carboxylate (21) (13.29 g, 64.8 mmol) in DMA (200 ml) were added 4-(methoxymethoxy)benzoic acid (11.8 g, 64.8 mmol) and EDC (14.90 g, 78 mmol). The resulting mixture was stirred for 18 hr at room temperature. Afterwards, the reaction mixture was concentrated, followed by addition of water (250 ml) and DCM (250 ml). The layers were separated and the organic layer was washed with water (100 ml), dried on $MgSO_4$ and concentrated in vacuo. The resulting solid material was transferred to a filter and rinsed with EtOAc (200 ml). The product ethyl 6-(4-(methoxymethoxy)

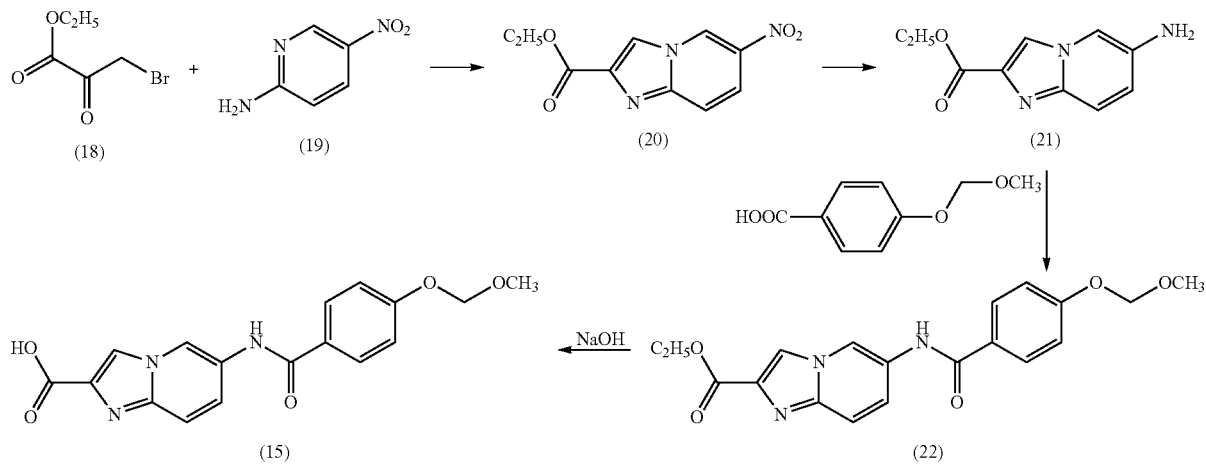

5-Nitropyridin-2-amine (19, 50 g, 359 mmol) was suspended in ethanol (700 ml, 99+%) and bubbled through with argon. Next, 1.1 equivalents of ethyl bromopyruvate (18, 79 ml, 503 mmol) were added and stirred for 45 min. Then, the reaction mixture was warmed at 85° C. for 6 hr, another 0.3 equivalents ethyl bromopyruvate (79 ml, 503 mmol) were added and warmed to 85° C. for 16 hr.

benzamido)imidazo[1,2-a]pyridine-2-carboxylate (22) was dried in vacuum. Compound (22) (22.16 g, 60 mmol) was dissolved in 1,4-dioxane (50 ml) and water (50 ml) followed by the addition of an aqueous 2M NaOH solution (100 ml, 200 mmol). The mixture was stirred at 70° C. for 30 min.

Next, the mixture was cooled to room temperature, and, after addition of water (50 nil) was added, acidified (using a 4M HCl solution). The resulting suspension was filtered and the solid material was dried to give 6-(4-(methoxymethoxy)benzamido)imidazo[1,2-a]pyridine-2-carboxylic acid (15) (12.1 g, 35.5 mmol, 59.1% yield) as a yellow/brown coloured solid. UPLC-MS confirmed that the correct product was formed.

Example 6a

Preparation of compound (17) from (14) and (15) according to the following scheme:

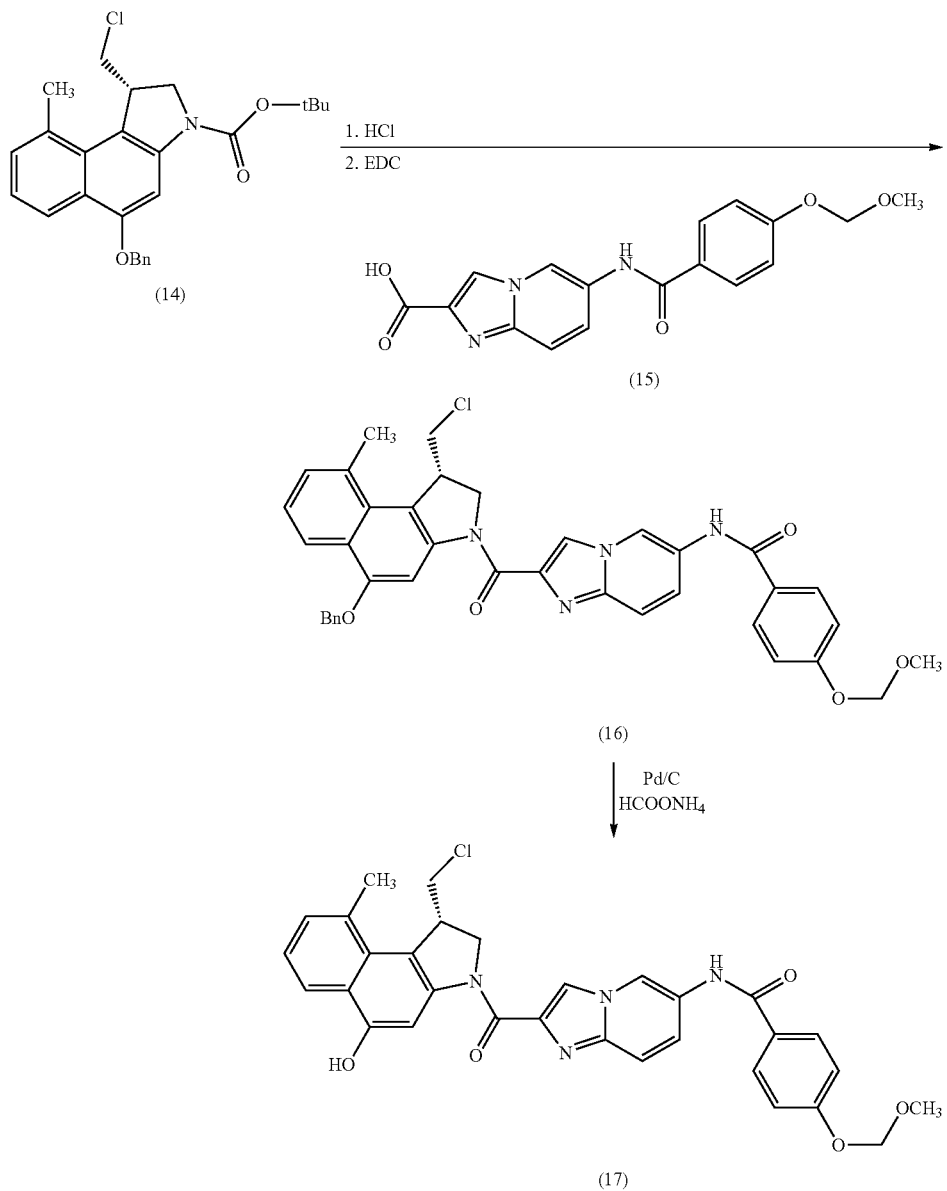

(S)-tert-Butyl 5-(benzyloxy)-1-(chloromethyl)-9-methyl-1H-benzo[e]indole-3(2H)-carboxylate (14) (4.5 g, 10.27 mmol) was dissolved in HCl/dioxane (4M, 30 ml) and stirred for 4 hr at 20° C. The resulting suspension was concentrated and dried in vacuo to yield a white/grey solid.

The obtained HCl-salt was then dissolved in DMA (80 ml), cooled to 0° C., 6-(4-(methoxymethoxy)benzamido) imidazo[1,2-a]pyridine-2-carboxylic acid (15) (3.86 g, 11.30 mmol) and EDC (5.91 g, 30.8 mmol) were added and stirred for 18 hr allowing the mixture to warm to 20° C.

Then, the reaction mixture was concentrated in vacuo, the crude product was dissolved in DCM/water (1200 ml, 1:1, v/v) and the layers were separated. The organic layer was dried on MgSO$_4$, filtered and concentrated. The crude product was purified by silica gel chromatography (eluent DCM with a gradient MeOH from 0 to 2.5%). Fractions with product were combined and concentrated to yield (S)—N-(2-(5-(benzyloxy)-1-(chloromethyl)-9-methyl-2,3-dihydro-1H-benzo[e]indole-3-carbonyl)imidazo[1,2-a]pyridin-6-yl)-4-(methoxy-methoxy)benzamide (16), (6.3 g, 9.53 mmol, 93% yield) as a white/grey solid. UPLC-MS indicated that the desired product was obtained.

A suspension of Pd/C (0.507 g, 0.476 mmol) in MeOH (20 ml) with 10 equivalents ammonium formate was heated to 95° C. for 5 min. Then, the mixture was allowed to cool to RT (20° C.). Next, 10 equivalents ammonium formate were added, followed by a suspension of (S)—N-(2-(5-(benzyloxy)-1-(chloromethyl)-9-methyl-2,3-dihydro-1H-benzo[e]indole-3-carbonyl)imidazo[1,2-a]pyridin-6-yl)-4-(methoxymethoxy)benzamide (16) (6.3 g, 9.53 mmol) in THF (100 ml). The resulting mixture was stirred for 3 hr at 20° C. After 100 minutes an additional 200 mg of Pd/C was added.

When the reaction was complete it was filtered over Hyflo filter aid and rinsed with THF (50 ml) followed by concentration. The crude product was purified by silica gel column chromatography (pre-packed on silica), eluting it with DCM with a gradient of MeOH (2.5 to 10%). The combined product fractions were concentrated and dried in vacuo to yield (S)—N-(2-(1-(chloromethyl)-5-hydroxy-9-methyl-2,3-dihydro-1H-benzo[e]indole-3-carbonyl)-imidazo[1,2-a]pyridin-6-yl)-4-(methoxymethoxy)benzamide (17) (4.9 g, 8.58 mmol, 90% yield) as a dark yellow solid. UPLC-MS indicated that the desired product was obtained.

Example 6b

Preparation of compound (17) from (14) and (15) according to the scheme of Example 6a:

In a jacketed reactor compound (14) (183 g, 0.418 mol) was suspended in a HCl/dioxane (4M, 2.08 L) solution and stirred at 28-32° C. for 3 hours. The formed suspension was cooled down to 18-22° C. and to which then methyl-t-butylether (0.76 L) was added. The formed solid was filtered off, washed with methyl-t-butylether (0.64 L) and dried at 40° C. in a rotary evaporator yielding the HCl-salt [(S)-5-(benzyloxy)-1-(chloromethyl)-9-methyl-2,3-dihydro-1H-benzo[e]indole hydrochloride] in 152.3 g (97.4% yield) (HPLC purity 98.08%).

The obtained HCl-salt (76.1 g, 0.203 mol) was suspended in DMA (1.25 L) in a jacketed reactor and compound (15) (74.3 g, 0.218 mol) was added. The temperature of the reaction mixture was adjusted to 18-22° C. and EDC (58.5 g, 0.305 mol) was added followed by DMA (0.2 L). The reaction mixture was stirred for 1 hour at 18-22° C. The temperature in the jacket was changed to 10° C. and ammonium hydroxide (6.8 ml) was added to the reaction mixture. Water (200 mL) was gradually added to the reaction mixture and the product started to crystallize. The solid product was filtered and washed with methanol (2×0.6 L). The product was re-slurried in methanol (1.2 L) and the suspension was stirred for 2 hours. The product was filtered and washed with methanol (0.2 L) and it was dried at 45-50° C. giving compound (16) (122 g, 89% yield).

Compound 16 (240 g, 0.363 mol) was suspended in THF (3.9 L) in a hydrogenation reactor. Meanwhile, Pd/C catalyst was activated by suspending 5% Pd/C (86.5 g, wet paste approx. 50%) catalyst in methanol and ammonium formate (257.5 g). The mixture was heated to 35° C. and stirred at this temperature for 15 minutes. The mixture was cooled down to 20° C. The catalyst suspension was added to the hydrogenation reactor. The reactor was flushed with nitrogen and stirring was switched on. The reaction mixture was stirred at 20° C. for 2.5 h. The catalyst was filtered off under nitrogen and was washed with THF (2×1 L). The filtrate was evaporated on a rotary evaporator at reduced pressure giving a solid residue. Dichloromethane (1.15 L) was added to the solid residue and the mixture was stirred to form a crystalline suspension. The product was filtered and washed with dichloromethane (0.5 L) and methanol (0.2 L).). The product was re-slurried in methanol (1 L), DMA (50 mL) was added and the suspension was stirred at 20° C. for 2 hours. The product was filtered, washed with methanol (250 mL) and dried. Compound (17), 167 g (80.6% yield) was obtained.

The invention claimed is:

1. A process comprising converting a compound of formula (I)

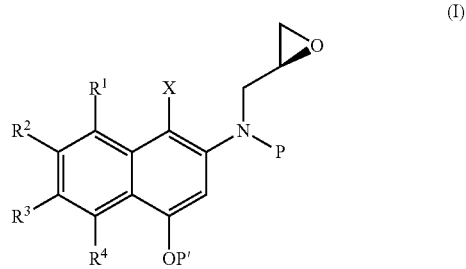

into a compound of formula (II)

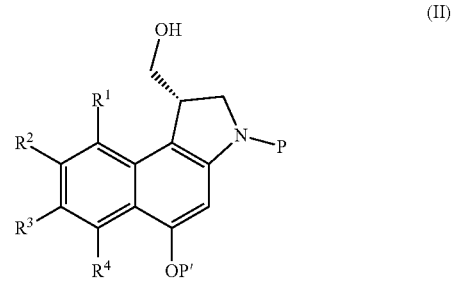

by reaction with a monometal organolithium reagent in a suitable solvent, wherein P and P' are independently protective groups, $R^1$ is $CH_3$, $CH_2CH_3$, $OCH_3$, $OCH_2CH_3$, $CF_3$, $OCF_3$, Cl or F, $R^2$, $R^3$, and $R^4$ are independently H or $C_{1-6}$ alkyl or $R^1$ and $R^2$ taken together form a 5- or 6-membered (hetero)cycloalkyl group and X is halogen.

2. The process according to claim 1, wherein $R^1$ is $CH_3$, $CH_2CH_3$, $OCH_3$ or $OCH_2CH_3$, $R^2$, $R^3$, and $R^4$ are independently H or $C_{1-6}$ alkyl or $R^1$ and $R^2$ taken together form a 5-membered (hetero)cycloalkyl group.

3. The process according to claim 1, wherein the monometal organolithium reagent is selected from the group consisting of n-butyl lithium, tert-butyl lithium and methyl lithium.

4. The process according to claim 1, wherein the halogen is bromine or iodine.

5. The process according to claim 1, wherein a strong base is added.

6. The process according to claim 1, further comprising converting the compound of formula (II) into a compound of formula (III)

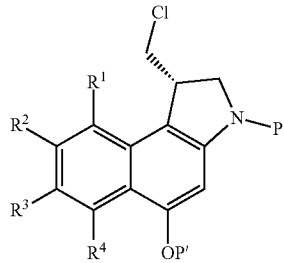
(III)

by either a one-step or two-step reaction with a chlorinating reagent, wherein $R^1$, $R^2$, $R^3$, $R^4$, P and P' are as defined in claim 1.

7. The process according to claim 6, wherein the chlorinating reagent is selected from the group consisting of LiCl, KCl, NaCl, NH$_4$Cl, HCl, AlCl$_3$ in concentrated HCl, PPh$_3$/CCl$_4$, PPh$_3$/NCS, SOCl$_2$ and PCl$_3$/PCl$_5$.

8. The process according to claim 7, wherein the chlorinating reagent is LiCl or PPh$_3$/CCl$_4$.

9. The process according to claim 6, further comprising converting the compound of formula (III) into a compound of formula (IV)

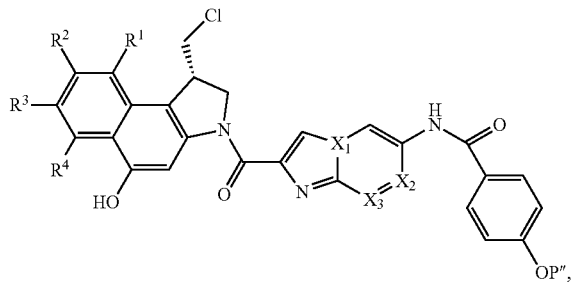
(IV)

by
a) removal of the P protective group from the compound of formula (III) and b) reaction of the unprotected compound of formula (III) with a compound of formula (V)

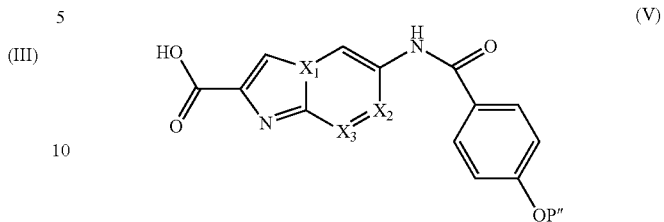
(V)

in the presence of a coupling reagent followed by
c) elimination of the P' protective group,
wherein $R^1$, $R^2$, $R^3$, $R^4$, P and P' are as defined in claim 6,
P'' is independently a protective group and
$X_1$, $X_2$, are $X_3$ are independently C or N.

10. The process according to claim 9, wherein the coupling reagent is selected from the group consisting of BOP, DCC, DIC, EDC, HATU, TBTU and T3P.

11. The process according to claim 10, wherein the coupling reagent is EDC.

12. The process according to claim 1, wherein the compound of formula (II) is

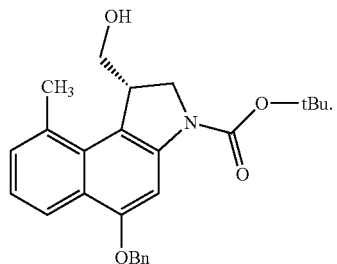 [SMILES: Cc1cccc2c(OCc3ccccc3)cc3c(c12)[C@H](CO)CN3C(=O)OC(C)(C)C]

13. The process according to claim 9, wherein the compound of formula (IV) is

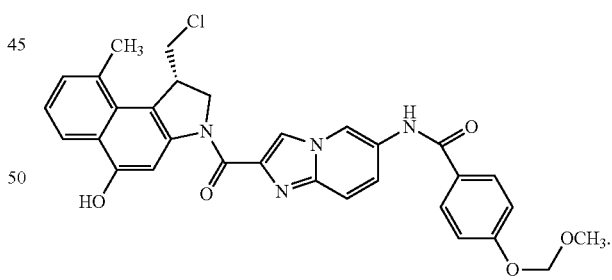

14. The process according to claim 9, further comprising isolating the compound of formula (IV).

* * * * *